United States Patent
Zimmerling et al.

(10) Patent No.: US 7,338,028 B2
(45) Date of Patent: Mar. 4, 2008

(54) FLUID SWITCH CONTROLLED TRANS-CUTANEOUSLY VIA MAGNETIC FORCE

(75) Inventors: Martin Zimmerling, Innsbruck (AT); Claude Jolly, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 236 days.

(21) Appl. No.: 10/726,066

(22) Filed: Dec. 2, 2003

(65) Prior Publication Data

US 2004/0256584 A1    Dec. 23, 2004

Related U.S. Application Data

(60) Provisional application No. 60/512,384, filed on Oct. 17, 2003, provisional application No. 60/430,252, filed on Dec. 2, 2002.

(51) Int. Cl.
    *F16K 7/04* (2006.01)
(52) U.S. Cl. ........................................................ 251/7
(58) Field of Classification Search ............. 604/890.1, 604/891.1, 167.02, 167.03, 167.05, 181, 604/183, 186, 246, 247, 248, 249, 256; 251/65, 251/7, 4
    See application file for complete search history.

(56) References Cited

U.S. PATENT DOCUMENTS

| | | | | |
|---|---|---|---|---|
| 3,731,670 A | * | 5/1973 | Loe | 128/843 |
| 3,777,737 A | * | 12/1973 | Bucalo | 128/843 |
| 4,207,554 A | | 6/1980 | Resnick et al. | 340/146.3 |
| 4,443,214 A | * | 4/1984 | Marion | 604/9 |
| 4,541,429 A | * | 9/1985 | Prosl et al. | 604/249 |
| 5,630,839 A | | 5/1997 | Corbett, III et al. | 607/137 |
| 5,643,194 A | * | 7/1997 | Negre | 604/8 |
| 5,800,500 A | | 9/1998 | Spelman et al. | 607/137 |
| 5,876,443 A | | 3/1999 | Hochmair et al. | 623/10 |

(Continued)

FOREIGN PATENT DOCUMENTS

DE    3242870 A1    6/1983

(Continued)

*Primary Examiner*—Nicholas D. Lucchesi
*Assistant Examiner*—Christopher Koharski
(74) *Attorney, Agent, or Firm*—Bromberg & Sunstein LLP (57) ABSTRACT

A fluid switch or valve for an implantable fluid delivery system is provided. The fluid switch or valve includes a fluid chamber having a fluid inlet and a fluid outlet and an internal magnet disposed within the fluid chamber. The internal magnet is moveable such that displacement of the internal magnet restricts the flow of fluid through the fluid chamber.

30 Claims, 6 Drawing Sheets

U.S. PATENT DOCUMENTS

| | | | |
|---|---|---|---|
| 5,891,183 A | 4/1999 | Zierhofer | 607/57 |
| 5,922,017 A | 7/1999 | Bredberg et al. | 607/137 |
| 5,983,139 A | 11/1999 | Zierhofer | 607/56 |
| 5,999,859 A | 12/1999 | Jolly | 607/137 |
| 6,066,088 A * | 5/2000 | Davis | 600/29 |
| 6,231,604 B1 | 5/2001 | Ilberg | 623/10 |
| 6,348,070 B1 | 2/2002 | Teissl et al. | 623/11.11 |
| 6,361,494 B1 | 3/2002 | Lindenthaler | 600/373 |
| 6,440,102 B1 | 8/2002 | Arenberg et al. | 604/96.01 |
| 6,535,153 B1 | 3/2003 | Zierhofer | 341/143 |
| 6,556,870 B2 | 4/2003 | Zierhofer et al. | 607/57 |
| 6,594,525 B1 | 7/2003 | Zierhofer | 607/57 |
| 6,600,955 B1 | 7/2003 | Zierhofer | 607/57 |
| 6,661,363 B2 | 12/2003 | Zierhofer | 341/143 |
| 6,727,833 B2 | 4/2004 | Zierhofer | 341/143 |
| 6,838,963 B2 | 1/2005 | Zimmerling et al. | 335/205 |
| 6,885,326 B2 | 4/2005 | Zierhofer | 341/143 |
| 6,966,325 B2 * | 11/2005 | Erickson | 137/1 |
| 2002/0019669 A1 | 2/2002 | Berrang et al. | 623/10 |
| 2002/0108623 A1 * | 8/2002 | Rehder et al. | 128/899 |
| 2004/0039245 A1 | 2/2004 | Jaeger et al. | 600/25 |
| 2004/0133250 A1 | 7/2004 | Ball | 607/57 |

FOREIGN PATENT DOCUMENTS

| | | |
|---|---|---|
| DE | 29513195 U1 | 12/1996 |
| DE | 19960131 A1 | 7/2001 |
| EP | 0564321 A2 | 6/1993 |
| WO | WO 81/00209 | 5/1981 |
| WO | WO 98/52640 | 11/1998 |

* cited by examiner

FLUID SWITCH CONTROLLED TRANS-CUTANEOUSLY VIA MAGNETIC FORCE

The present application claims priority from U.S. Provisional Application Ser. No. 60/430,252, filed Dec. 2, 2002 and U.S. Provisional Application Ser. No. 60/512,384, filed Oct. 17, 2003. Both of the aforementioned provisional applications are hereby incorporated herein, in their entireties, by reference.

TECHNICAL FIELD

The present invention relates to implantable electronic devices and more particularly, to an implantable valve device.

BACKGROUND ART

Fluid delivery systems and apparatuses are often used to provide pharmaceuticals to the body of a human or animal subject. For example, one or more liquid drugs may be delivered to the inner ear and passive or active diffusion of the liquid drug may be used to treat inner ear functions.

Such systems and apparatuses may include devices for controlling fluid flow and catheters for fluid delivery. For example, U.S. Pat. No. 6,440,102 discloses an apparatus for delivering fluid materials into and out of the inner ear via the round window membrane. The apparatus includes a fluid transfer conduit having one or more passageways which may have a semi-permeable membrane associated therewith to control fluid flow. Attached to the conduit is an inflatable bladder which, when inflated, engages the internal side wall of the round window niche, thereby securing the bladder and part of the conduit within the niche. The conduit can then transfer fluids to and from the niche and the fluid-permeable round window membrane therein.

SUMMARY OF THE INVENTION

In a first embodiment of the invention, a valve or fluid switch for a fluid delivery system is provided. The fluid delivery system is capable of being implanted in a living subject, for example, the fluid delivery system may be part of a cochlear implant. The valve includes a fluid chamber having a fluid inlet and a fluid outlet and an internal magnet disposed within the fluid chamber. The internal magnet is moveable such that displacement of the internal magnet restricts the flow of fluid through the fluid chamber. The valve may also include an external magnet disposed on the skin of the subject. The external magnet provides a magnetic field for displacing the internal magnet such that fluid flow through the fluid chamber is restricted when the internal magnet occupies a first position and fluid flow through the fluid chamber is not restricted when the internal magnet occupies a second position.

In accordance with related embodiments, the external magnet may be rotatable. The fluid chamber may be implanted in a subject's ear or in another part of a subject's skull. Further, the internal magnet may be formed from a biocompatible material. In accordance with other related embodiments the fluid chamber may include a first anchor and a second anchor for preventing rotation of the internal magnet. The anchors may be formed from a ferromagnetic material. Further, the fluid chamber may be formed from a non-ferromagnetic material.

In accordance with further related embodiments, the internal magnet may be spherical or cylindrical, the fluid chamber may include an anchor for securing the internal magnet in the fluid chamber and one pole of the internal magnet may include one or more grooves for permitting fluid flow through the fluid chamber when the internal magnet is secured by the anchor. The internal magnet may be coated with a non-ferromagnetic material, for example, the internal magnet may be coated with silicone. When the internal magnet is coated, the coating at one pole of the internal magnet may include one or more grooves for permitting fluid flow through the fluid chamber when the internal magnet is secured by the anchor. Alternatively, one pole of the internal magnet may include a recess for permitting fluid flow through the fluid chamber when the internal magnet is secured by the anchor. Further, one pole of the internal magnet may be replaced with or include semi-permeable material for permitting fluid flow through the chamber when the internal magnet is secured by the anchor. The anchor may be formed of a ferromagnetic material.

In accordance with other embodiments, the valve or fluid switch may further include an external indicator for checking the displacement of the internal magnet, and the external indicator may include a compass. In accordance with further embodiments, the external magnet may include a first magnet having a magnetic moment oriented in a first direction and a second magnet having a magnetic moment oriented in a second direction such that the external magnet automatically aligns with the internal magnet. The first magnet may be cylindrical and the second magnet may be ring-shaped. Alternatively, the external magnet may be confined in a housing wherein the external magnet is capable of experiencing horizontal displacement such that it automatically aligns with the internal magnet.

In accordance with another embodiment of the invention, the valve or fluid switch for an implantable fluid delivery system may includes a fluid chamber including a catheter having a fluid inlet and a fluid outlet and an internal magnet disposed within the fluid chamber. The internal magnet is moveable such that displacement of the internal magnet restricts the flow of fluid through the catheter. In a related embodiment, an external magnet may be disposed on the skin of a subject wherein the external magnet provides a magnetic field for displacing the internal magnet such that fluid flow through the catheter is restricted when the internal magnet occupies a first position and fluid flow through the catheter is not restricted when the internal magnet occupies a second position.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

Figure 1:
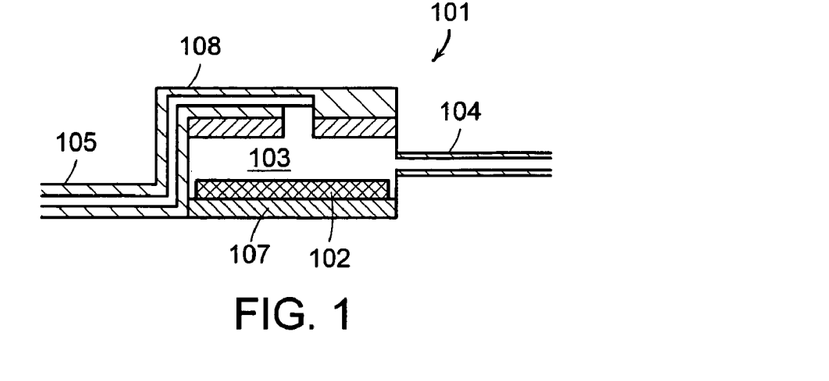
FIG. 1 is graphical illustration of a fluid switch or valve in accordance with one embodiment of the present invention.
Figure 2:
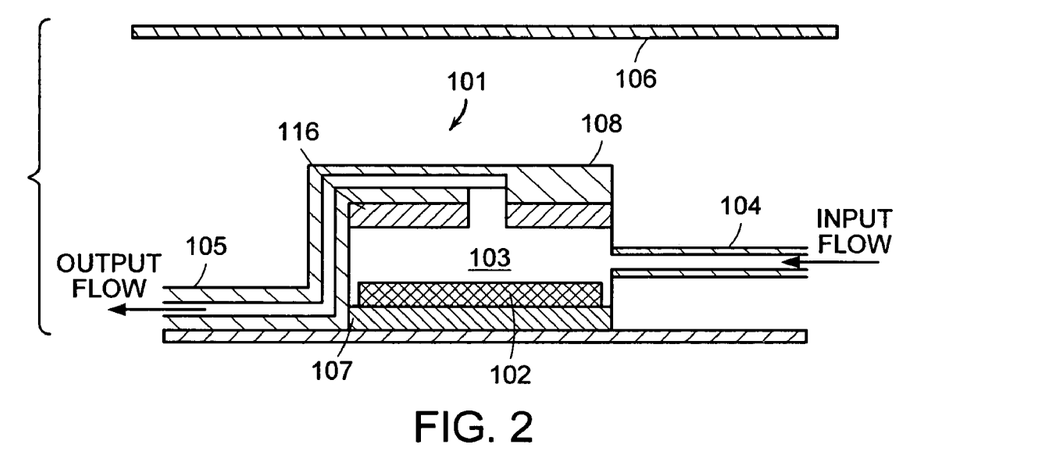
FIG. 2 is a graphical illustration of the fluid valve of FIG. 1 in an open (or ON) position.

FIGS. 1 and 2 are graphical illustrations showing an ON/OFF valve (or fluid switch) used to interrupt and resume fluid flow in an implantable fluid delivery system or other fluid system. The valve 101 includes an internal but movable biocompatible magnet 102 located in a non-ferromagnetic chamber 103. The chamber 103 includes an inlet catheter 104 and an outlet catheter 105. The internal magnet 102 may be displaced to an open (ON) or closed (OFF) position by an external magnetic force applied at the surface of a subject's skin 106. In accordance with the embodiments of FIGS. 1 and 2, the valve (or switching) state is controlled by the orientation of the external magnetic field.

The internal magnet 102 may be encapsulated by a gold film or other material (e.g. metal and/or polymer) to provide a biocompatible interface with the surrounding fluid or gas. The shape of the internal magnet 102 (or non-ferromagnetic case or housing 108 which contains one magnet or several magnets of any shape) may be a disk, a cube, a rectangle, a cylinder, a sphere, or any other shape.

Figure 3:
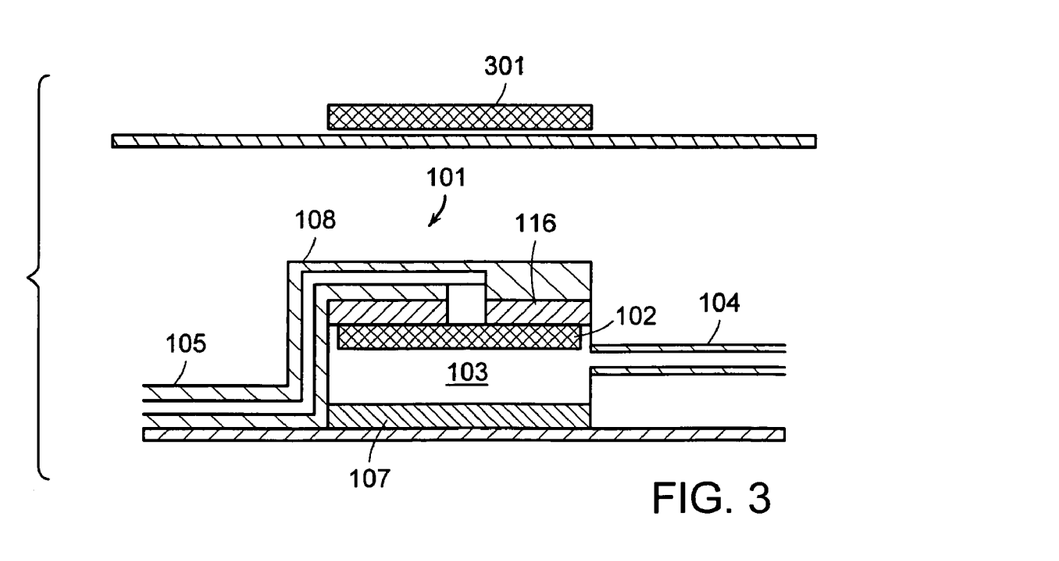
FIG. 3 is a graphical illustration of a fluid switch or valve in a closed (or OFF) position due to an external magnet located on the skin in accordance with another embodiment of the invention.

FIG. 3 is a graphical illustration of a fluid valve in a closed (OFF) position due to an external magnet 301 located on the skin. The external magnet 301 attracts the internal magnet 102 of the fluid chamber 103 and causes closure of the fluid flow, thus bi-stable valve positions are provided. The internal magnet 102 may move, but it cannot turn and hence cannot change the axis of its magnetic momentum vector. Such an arrangement requires two anchors 116 and 107 one anchor 116 on the side facing the skin (i.e. lateral side) and a second anchor 107 on the opposite side (i.e. medial side). As shown in FIGS. 1 and 2, in the absence of an external magnetic field the internal magnet 102 is dominantly attracted by that anchor 107 which is closer and the internal magnet 102 is caught in a stable position. Switching between these two stable positions can be achieved by applying an external magnetic field (such as by holding external magnet 301 over the skin). Depending on the orientation of the external magnetic field, the internal magnet 102 will either be attracted or repelled by the external field and thus will be pushed to the medial position or pulled to the lateral position. After removing the external magnet 301 (or switching off the external magnetic field) the internal magnet 102 keeps its stable position.

Figure 4:
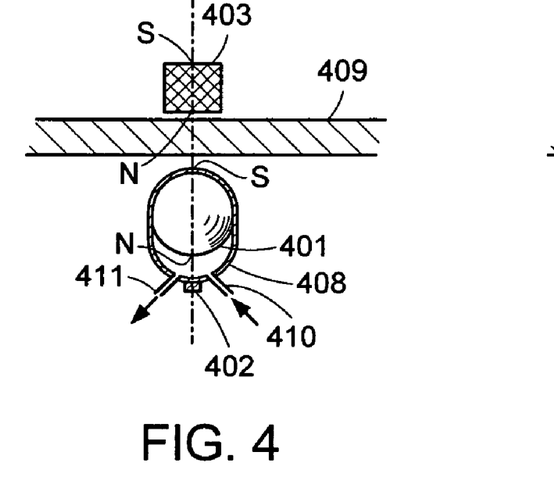
FIG. 4 is a graphical illustration of a fluid switch or valve with a movable magnet in accordance with another embodiment of the invention.
Figure 5:
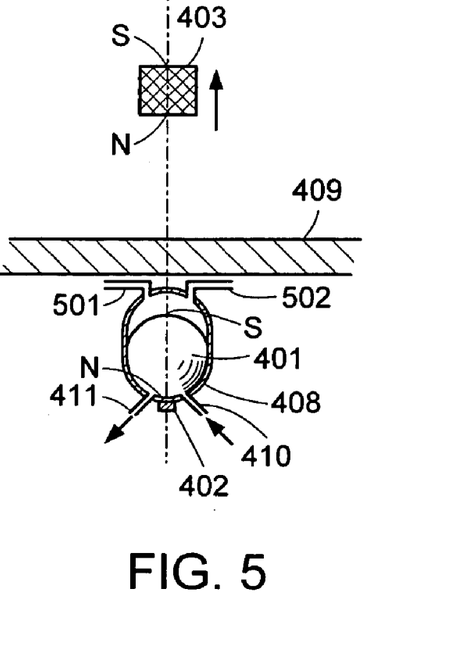
FIG. 5 is a graphical illustration of the fluid valve of FIG. 4 in a closed (or OFF) position.

FIGS. 4 and 5 are graphical illustrations of a fluid valve with a movable internal magnet 401 in accordance with another embodiment of the invention. In accordance with the embodiment of FIG. 4, the valve is mono-stable. Mono-stability may be achieved by a small piece of ferromagnetic material 402 (also called an anchor), which is located on the housing 408 at the side opposite to the skin (i.e. medial side). When no external field is present, the magnet is attracted by the anchor 402 and fixed in that position as shown in FIG. 5. Without the anchor 402, the internal magnet 401 would not be held stable in its position and orientation during the absence of an external magnetic field. Such an arrangement may be exploited to interrupt or resume a fluid flow between the fluid inlet 410 and fluid outlet 411. When an external magnetic field with correct orientation is present (such as by holding an external magnet 403 at the surface of the skin 409, or by generating a magnetic field with means of a current-driven electric coil) this magnetic field generates a stronger attractive force than the anchor 402, and the internal magnet 401 is pulled towards the skin and thus can resume a fluid flow. The size of the ferromagnetic anchor 402 defines the stability of the switching state: The bigger the anchor 402, the more robust the valve against vibration or mechanical shock and the external magnetic field needs to be stronger be to attract the internal magnet.

Thus, in accordance with embodiments of the invention, the fluid valve may include two stable valve (or fluid switching) positions and two unstable valve positions. The internal magnet 401 may move along a particular axis and also can turn, thus changing the axis of its magnetic momentum vector. Such movement may be achieved with a spherical magnet as shown in FIGS. 4 and 5. As described above, an anchor 402 on the medial side of the encapsulation allows fixation of the internal magnet 401 during the absence of an external magnetic field, and two stable valve (or switching) states are possible. Additionally, two unstable valve states are possible during the presence of an external magnetic field. As shown in FIG. 5, exploiting these unstable valve states (when either the north pole or the south pole of the internal magnet 401 is facing the skin 409) requires an additional inlet 501 and outlet 502 on the side of the housing 408 which faces the skin flap 409.

The internal magnet 401 may be free to move along a particular axis, free to turn in any direction and/or free to move and turn in a variety of manners. Similarly, the internal magnet 401 may be free to turn into any direction that is safe in the presence of strong external magnetic fields like those produced as a result of MRI (Magnetic Resonance Imaging). The internal magnet 401 may align with the external magnetic field without exerting a torque to the housing 408 of the implant, and when the internal magnet 401 is aligned it cannot demagnetize.

Figure 6:
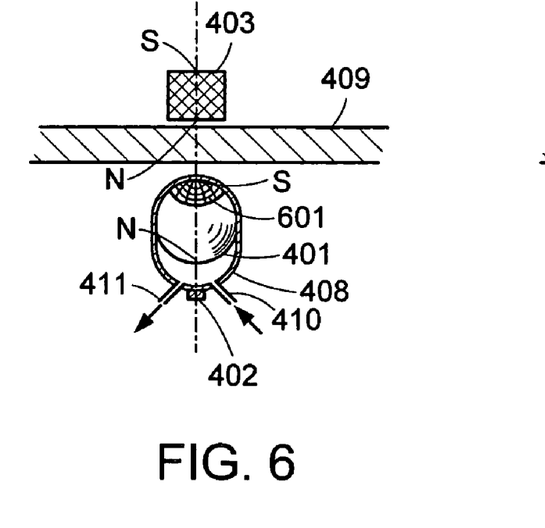
FIG. 6 is graphical illustration of a fluid switch or valve with a grooved magnet in accordance with a further embodiment of the invention.
Figure 7:
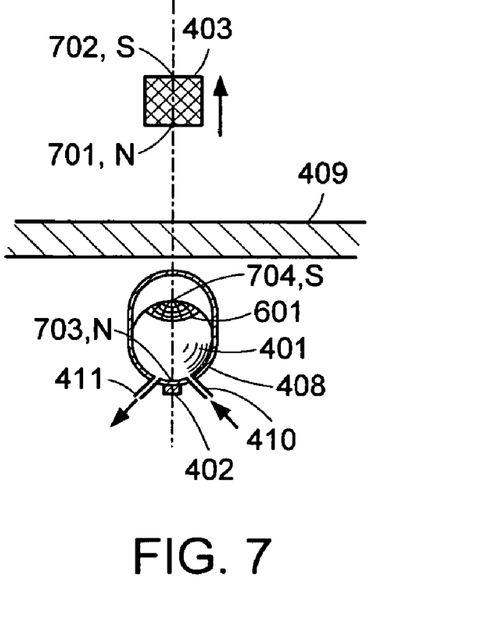
FIG. 7 is a graphical illustration of the fluid valve of FIG. 6 in a stable closed (or OFF) position.
Figure 8:
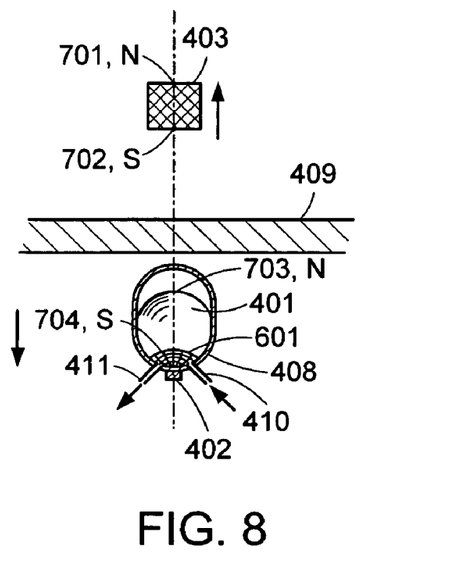
FIG. 8 is a graphical illustration of the fluid valve of FIG. 6 in a stable open (or ON) position.

FIG. 6 is graphical illustration of a fluid valve (or fluid switch) with a grooved magnet in accordance with a further embodiment of the invention. In accordance with this embodiment, one pole of the internal magnet 401 (or its coating) includes grooves 601 that are made in the coating to enable fluid flow when that magnetic pole is located over the fluid inlet 410 and outlet 411. As shown in FIG. 7, when the external magnet 403 is removed after having placed the north pole 701 of the external magnet 403 on the skin flap 409, the north pole 703 of the internal magnet 401, which does not have grooves, is attracted by the anchor 402. Fluid flow between the fluid inlet 410 and fluid outlet 411 is thus interrupted by the internal magnet 401. FIG. 8 is an illustration showing that by removing the external magnet 403 after having placed the south pole 702 of the external magnet 403 onto the skin, the south pole 704 of the internal magnet 401, which includes grooves 601, is attracted to the anchor 402 and fluid may flow through the grooves 601 between the fluid inlet 410 and fluid outlet 411.

Figure 9:
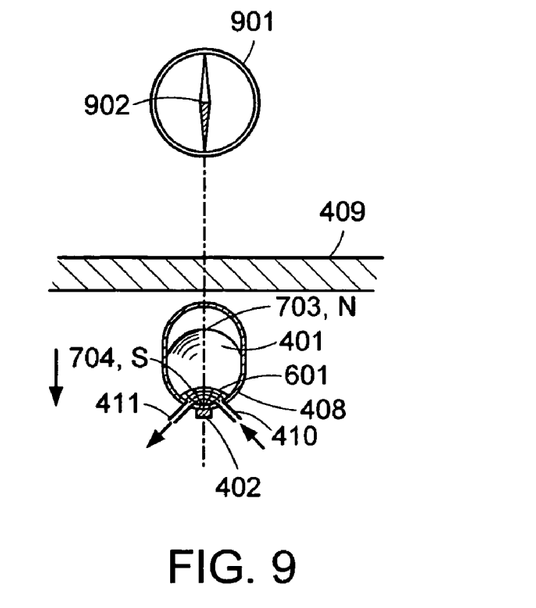
FIG. 9 is a graphical illustration of a fluid switch or valve including an indicator for checking the state of the fluid switch in accordance with another embodiment of the invention.

FIG. 9 is a graphical illustration of a fluid valve (or fluid switch) including an indicator for checking the state of the fluid switch in accordance with another embodiment of the invention. The indicator may be a compass 901 with a needle 902 that aligns with the poles 703 and 704 of the internal magnet 401 in such a manner as to indicate the orientation of the magnetic field and thus the position of the poles. For example, the needle 902 of the compass 901 will indicate that the north pole 703 of the internal magnet 401 is closer to the skin flap 409 and that the south pole 704 (having the grooves 601) is over the fluid inlet and outlet 410 and 411. In accordance with this embodiment, when the internal magnet is in this position, the fluid switch is open (or ON), and fluid flow is allowed. Labeling of the compass needle 902 may also indicate the actual switching or valve state.

Figure 10:
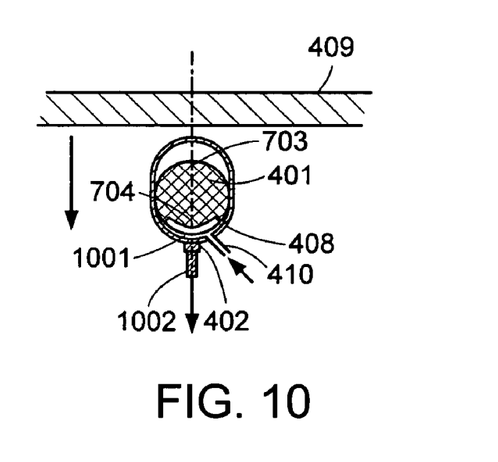
FIG. 10 is a graphical illustration of a fluid switch or valve in which coating over one magnetic pole is recessed or replaced in accordance with a further embodiment of the invention.

FIG. 10 is a graphical illustration of a fluid valve (or fluid switch) in which coating over one magnetic pole is recessed or replaced in accordance with a further embodiment of the invention. In accordance with this embodiment, the coating over one pole of the internal magnet 401 (here the south pole 704) is recessed or replaced with a semi-permeable material 1001. In this manner, fluid may flow between the fluid inlet 410 and fluid outlet 1002 when this particular pole is over the fluid inlet 410 and outlet 1002. Additionally, the embodiment of FIG. 10 may allows the implementation of open/closed (or ON/OFF) switching of fluid flow, switching between different fluid flow rates, switching of flow direction (see FIG. 13) and/or switching between different semi-permeable states (be incorporating filters or semi-permeable materials). Thus, the embodiment of FIG. 10 may be used as a fluid or gas pressure limiter to permit switching between different pressure levels.

Figure 11:
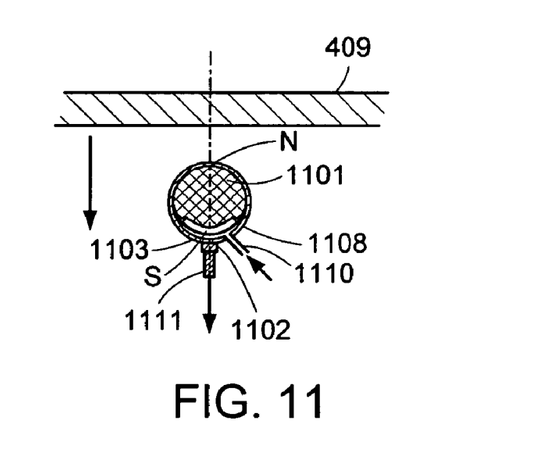
FIG. 11A is a graphical illustration of an example of a spherical or cylindrical magnet or coating that is recessed over one pole.
Figure 11A:
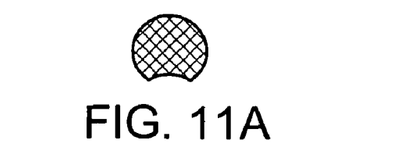

FIG. 11 is a graphical illustration of a bi-stable fluid valve (or fluid switch) in accordance with another embodiment of the invention. FIG. 11A is a graphical illustration of an example of a spherical or cylindrical magnet or coating that is recessed over one pole. In accordance with this embodiment, bi-stable valve or switching positions are accomplished with a freely turnable internal magnet 1101 having the coating over one of its poles recessed or replaced with a semi-permeable material 1103. The internal magnet 1101 cannot move inside its housing or containment 1108. This allows two stable valve or switching positions, and switching can be achieved by placing a magnet over the skin for a short time. The embodiments of FIGS. 11 and 11A also permit open/closed (or ON/OFF) switching of fluid flow, switching between different flow rates, switching of flow direction and/or switching between different semi-permeable states (by incorporating filters or semi-permeable materials).

Figure 12A:
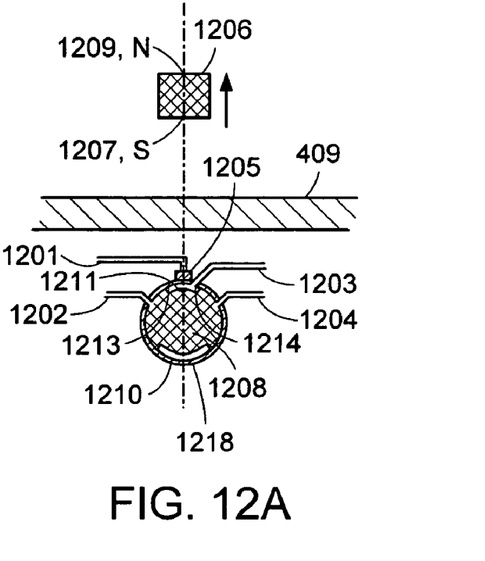
FIGS. 12A and 12B are graphical illustrations showing the effect of a fluid switching state of a fluid valve in accordance with an embodiment of the invention.
Figure 12B:
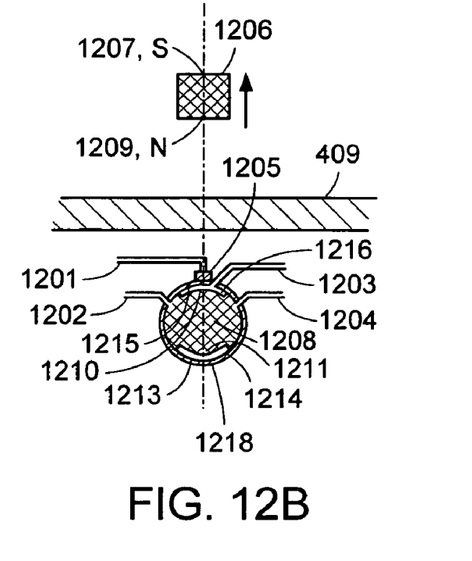

FIGS. 12A and 12B are graphical illustrations showing the effect of a valve or switching state of a fluid valve in accordance with an embodiment of the invention. In accordance with this embodiment, a freely turnable spherical or cylindrical internal magnet 1208 is encapsulated in a hermetical non-ferromagnetic housing 1218. The coating at poles 1210 and 1211 of the internal magnet 1208 are recessed. The anchor 1205 is placed on the lateral side (close to the skin flap 409) or at any other place on the housing 1218 instead of at the medial side. Further, switching is performed between more than one inlet and outlet. For example, switching is performed between inlets 1203 and 1204 and outlets 1201 and 1202. When external magnet 1206 is removed after having been placed such that the south pole 1207 of the external magnet 1206 was in contact with the skin flap 409, the north pole 1211 of the internal magnet 1208 is closer to the skin flap 409 and recesses 1213 and 1214 permit fluid flow between fluid inlet 1203 and fluid outlet 1201. When external magnet 1206 is removed after having been placed such that the north pole 1209 of the external magnet 1206 was in contact with the skin flap 409, the south pole 1210 of the internal magnet 1208 is closer to the skin flap 409 and recesses 1215 and 1216 permit fluid flow between fluid inlet 1204 and fluid outlet 1202. A crossover/crossfeed valve may also be implemented in accordance with this embodiment.

Figure 13:
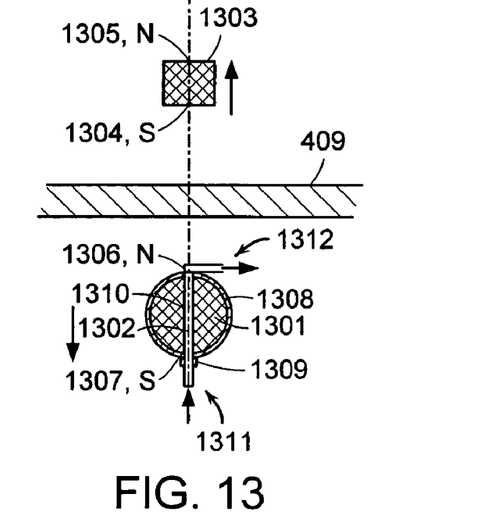
FIG. 13 is an graphical illustration of a magnetically activated implantable fluid switch or valve in accordance with another embodiment of the invention.

FIG. 13 is a graphical illustration of a magnetically activated implantable fluid valve or fluid switch in accordance with another embodiment of the invention. In accordance with this embodiment, a freely turnable spherical magnet 1301 in a non-ferromagnetic hermetic encapsulation or housing 1308 includes a bore 1302 and one-directional valve 1310. Since the valve 1310 in the internal magnet 1301 is one directional, the orientation of the internal magnet 1301 determines whether fluid flows into the bore 1302 at the medial side 1311 of the internal magnet 1301 and out of the bore 1302 at the lateral side 1312 of the internal magnet 1301 or vice versa. When external magnet 1303 is removed after having been placed such that the south pole 1304 of the external magnet 1303 was in contact with the skin flap 409, the north pole 1306 of the internal magnet 1301 is closer to the skin flap 409 and the internal magnet 1301 is attracted by the anchor 1309. Fluid flows into the bore 1302 from the medial side 1311 and out of the bore 1302 at the lateral side 1312. When external magnet 1303 is removed after having been placed such that the north pole 1305 of the external magnet 1303 was in contact with the skin flap 409, the south pole 1307 of the internal magnet 1301 is closer to the skin flap 409 and fluid flows into the bore 1302 from the lateral side 1312 of the internal magnet 1301 and out of the bore 1302 at the medial side 1311.

Figure 14:
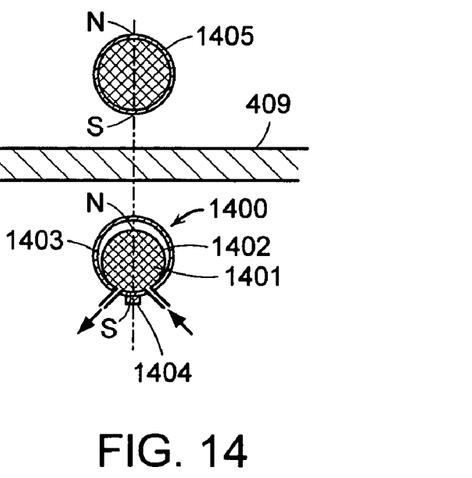
FIG. 14 is a graphical illustration of a magnetically driven fluid pump in accordance with a further embodiment of the invention.

FIG. 14 is a graphical illustration of a magnetically driven fluid pump in accordance with a further embodiment of the invention. In accordance with this embodiment, an ON/OFF valve (or fluid switch) and pump are used to interrupt and resume fluid flow in a fluid delivery system. The pump 1400 includes an internal magnet 1401 which is embedded in an excentrical, freely turnable and biocompatible body ("rotor") which together with a hermetically tight membrane 1402 separates the volume inside a non-ferromagnetic chamber 1403 into two parts. The rotor is fixed stable by a small ferromagnetic part 1404 ("anchor") during the absence of an external magnetic field. Thus, the flow valve is closed. The pump 1400 can be magnetically activated and driven by a rotating external magnetic field such as that provided by external rotating magnet 1405 (or an arrangement of solenoids). In this manner, fluid flow direction and the fluid flow rate may be controlled.

Figure 15:
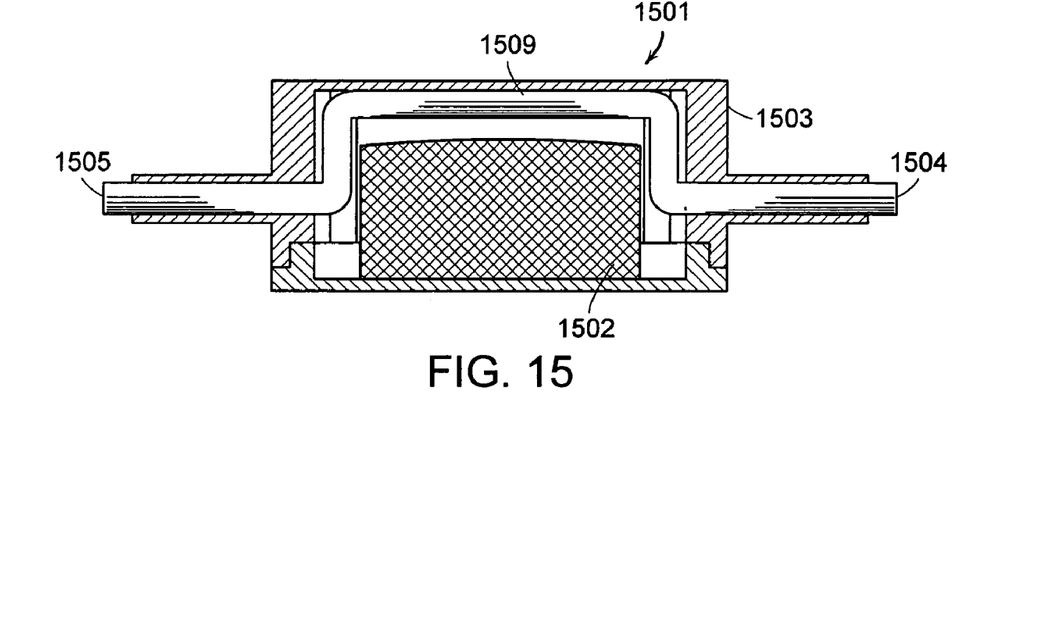
FIG. 15 is a graphical illustration of a fluid switch or valve with includes an internal catheter in accordance with another embodiment of the invention.
Figure 16:
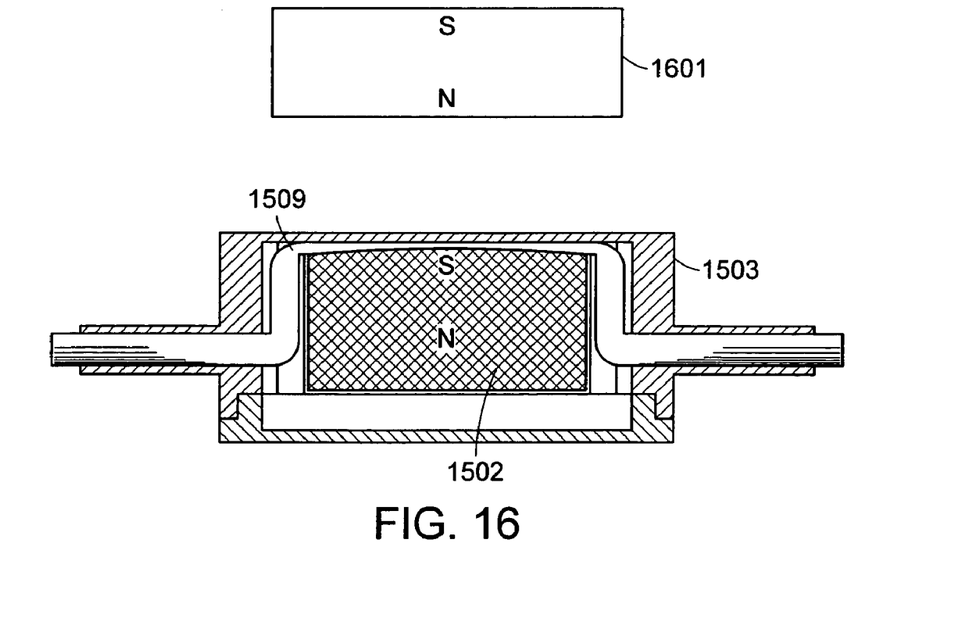
FIG. 16 is a graphical illustration of the embodiment of FIG. 15 wherein flow through the internal catheter is interrupted.

FIG. 15 is a graphical illustration showing a fluid valve or fluid switch which includes an internal catheter in accordance with another embodiment of the invention. Here again, the valve 1501 includes an internal but movable biocompatible magnet 1502 located in a non-ferromagnetic chamber. The chamber includes an internal catheter 1509 having an inlet 1504 and an outlet 1505. The internal magnet 1502 may be displaced so as to create an open (ON) position, wherein flow through the internal catheter 1509 is not interrupted or a closed (OFF) position wherein flow through the internal catheter 1509 is interrupted as shown in FIG. 16. As in the embodiment of FIG. 1, the internal magnet 1502 may be encapsulated by a gold film or other material (e.g. metal and/or polymer) to provide a biocompatible interface with the surrounding fluid or gas. The shape of the internal magnet 1502 (or non-ferromagnetic case or housing 1503 which contains one magnet or several magnets of any shape) may be a disk, a cube, a rectangle, a cylinder, a sphere, or any other shape.

FIG. 16 is a graphical illustration of a fluid valve or fluid switch in a closed (OFF) position due to an external magnet 1601 located on the skin. The external magnet 1601 attracts the internal magnet 1502 of the fluid chamber 1503. Consequently, the internal magnet 1502 squeezes the internal catheter 1509 and fluid flow through the internal catheter 1509 is interrupted.

Figure 17:
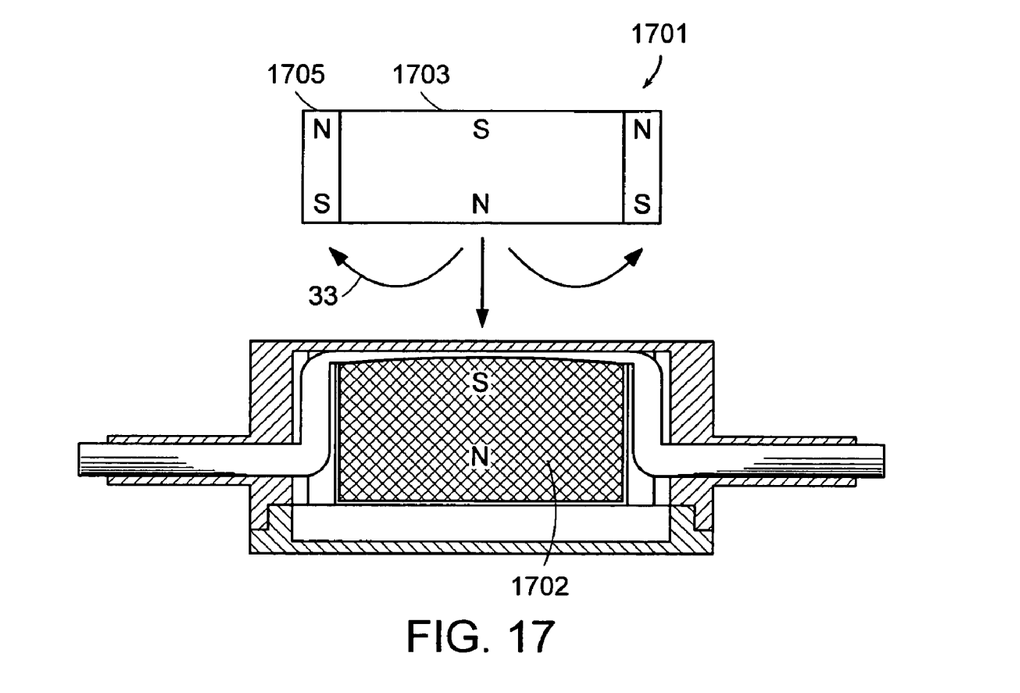
FIG. 17 is graphical illustration of a fluid switch or valve having a self-aligning external magnet in accordance with a further embodiment of the invention.

FIG. 17 is graphical illustration of a fluid valve or fluid switch having a self-aligning external magnet in accordance with a further embodiment of the invention. In accordance with this embodiment, the fluid valve includes an external magnet 1701 having a quadru-polar magnetic momentum. This is accomplished in that the external magnet 1701 includes an arrangement of two or more magnets with their magnetic moments oriented in different direction. Such an arrangement provides improved self-aligning (or self-centering) properties of external magnet 1701 over an implanted magnet 1702. In accordance with the arrangement shown in FIG. 17, the external magnet 1701 includes a cylindrical magnet 1703 and a ring-shaped magnet 1705 with opposite magnetization.

Figure 18:
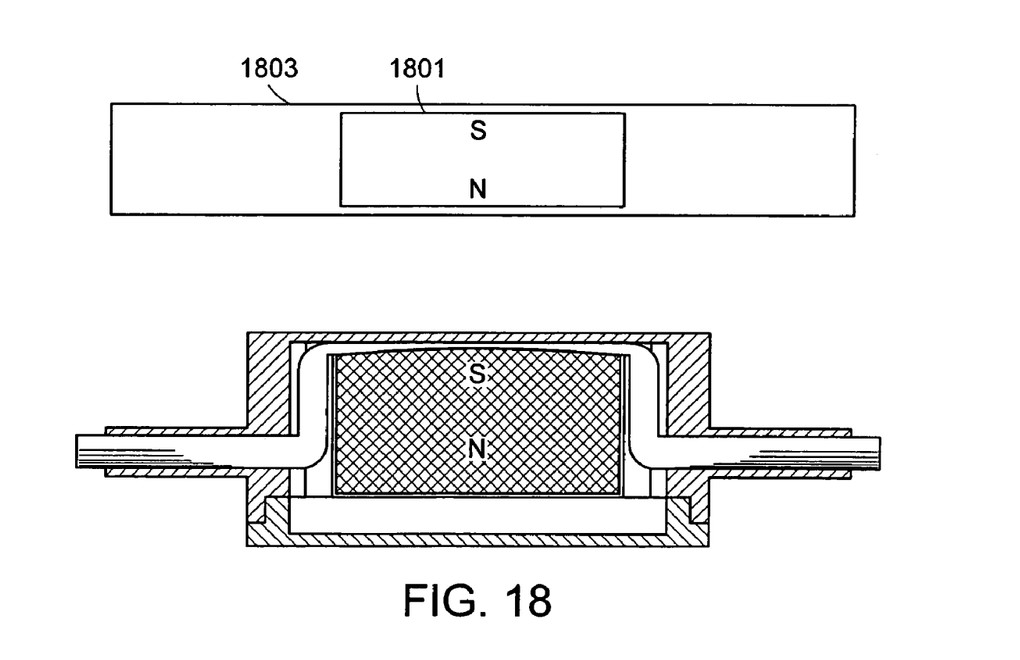
FIG. 18 is a graphical illustration of a fluid switch or valve having a self-aligning external magnet in accordance with another embodiment of the invention.

FIG. 18 is a graphical illustration of a fluid valve or fluid switch having a self-aligning external magnet in accordance with another embodiment of the invention. In accordance with the embodiment of FIG. 18, the fluid valve is provided with an external magnet 1801 that is confined in a box 1803 housing such that the external magnet 1801 is mechanically free to move horizontally (i.e., normal to its axis of magnetization). In this manner, precise alignment of the external magnet with an implanted magnet is permitted, even if the box or housing 1803 is not exactly placed over the implanted magnet.

Embodiments of the invention may be used for systems or applications other than human drug delivery. For example, the valves or fluid switches of the invention may be applied in biomedical engineering in general, automotive, domestic technique or other industries. Similarly, the embodiments of the invention may be used to magnetically control the flow of liquids and gases. Further, the external magnetic field can originate from an electro-magnet (current-driven coil) instead of a permanent magnet. Valves or fluid switches as described above may further be used to close a pump system while refilling a fluid reservoir and such valves or fluid switches may be used with an osmotic pump.

While the invention has been described in connection with specific embodiments thereof, it will be understood that it is capable of further modification. This application is intended to cover any variation, uses, or adaptations of the invention and including such departures from the present disclosure as come within known or customary practice in the art to which invention pertains.

What is claimed is:

1. A valve for an implantable fluid delivery system comprising:
    a fluid chamber having a fluid inlet and a fluid outlet; and
    an internal magnet disposed within the fluid chamber, the internal magnet having a north pole and a south pole forming a magnetic momentum vector axis wherein one pole of the internal magnet includes one or more grooves for permitting fluid flow through the fluid chamber when the one pole is located over the fluid inlet and the fluid outlet, the internal magnet movable such that the magnetic momentum vector axis is changed, the internal magnet being moveable such that displacement of the internal magnet restricts the flow of fluid through the fluid chamber.

2. A valve according to claim 1, further comprising:
    an external magnet for disposition on the skin of a subject, the external magnet providing a magnetic field for displacing the internal magnet such that fluid flow through the fluid chamber is restricted when the internal magnet occupies a first position and fluid flow through the fluid chamber is not restricted when the internal magnet occupies a second position.

3. A valve according to claim 2, wherein the external magnet is rotatable.

4. A valve according to claim 2, wherein the external magnet includes a first magnet having a magnetic moment oriented in a first direction and a second magnet having a magnetic moment oriented in a second direction such that the external magnet automatically aligns with the internal magnet.

5. A valve according to claim 4, wherein the first magnet is cylindrical and the second magnet is ring-shaped.

6. A valve according to claim 2, wherein the external magnet is confined in a housing such that the external magnet is capable of experiencing horizontal displacement such that it automatically aligns with the internal magnet.

7. A valve according to claim 1, wherein the fluid chamber is capable of implantation in a subject's ear or part of a subject's skull.

8. A valve according to claim 1, wherein the internal magnet is formed from a biocompatible material.

9. A valve according to claim 1, wherein the fluid chamber includes a first anchor and a second anchor for preventing rotation of the internal magnet.

10. A valve according to claim 9, wherein the anchors are formed from a ferromagnetic material.

11. A valve according to claim 1, wherein the fluid chamber is formed from a non-ferromagnetic material.

12. A valve according to claim 1, wherein the internal magnet is spherical.

13. A valve according to claim 1, wherein the internal magnet is cylindrical.

14. A valve according to claim 1, wherein the fluid chamber includes an anchor for securing the internal magnet in the fluid chamber.

15. A valve according to claim 14, wherein the internal magnet is coated at one pole with a non-ferromagnetic material.

16. A valve according to claim 15, wherein the coating includes the one or more grooves for permitting fluid flow through the fluid chamber when the internal magnet is secured by the anchor.

17. A valve according to claim 14, wherein one pole of the internal magnet includes a recess for permitting fluid flow through the fluid chamber when the internal magnet is secured by the anchor.

18. A valve according to claim 14, wherein one pole of the internal magnet includes a semi-permeable material for permitting fluid flow through the fluid chamber when the internal magnet is secured by the anchor.

19. A valve according to claim 14, wherein the anchor is formed of a ferromagnetic material.

20. A valve according to claim 1, wherein the internal magnet is coated with a non-ferromagnetic material.

21. A valve according to claim 20, wherein the non-ferromagnetic material is silicone.

22. A valve according to claim 1, further comprising an external indicator for checking an orientation of a magnetic field of the internal magnet.

23. A valve according to claim 22, wherein the external indicator includes a compass.

24. A valve according to either of claims 1 or 2, wherein the fluid delivery system is includes a cochlear implant.

25. A valve according to claim 1, wherein the fluid chamber includes a catheter having the fluid inlet and the fluid outlet and wherein the internal magnet is moveable such that displacement of the internal magnet restricts the flow of fluid through the catheter.

26. A valve according to claim 25, further comprising:
an external magnet for disposition on the skin of a subject, the external magnet providing a magnetic field for displacing the internal magnet such that fluid flow through the catheter is restricted when the internal magnet occupies a first position and fluid flow through the catheter is not restricted when the internal magnet occupies a second position.

27. A fluid switch for an implantable fluid delivery system comprising:
a fluid chamber having a fluid inlet and a fluid outlet; and
an internal magnet disposed within the fluid chamber, the internal magnet having a north pole and a south pole forming a magnetic momentum vector axis wherein one pole of the internal magnet includes one or more grooves for permitting fluid flow through the fluid chamber when the one pole is located over the fluid inlet and the fluid outlet, the internal magnet movable such that the magnetic momentum vector axis is changed, the internal magnet being moveable such that displacement of the internal magnet restricts the flow of fluid through the fluid chamber.

28. A fluid switch according to claim 27, further comprising:
an external magnet for disposition on the skin of a subject, the external magnet providing a magnetic field for displacing the internal magnet such that fluid flow through the fluid chamber is restricted when the internal magnet occupies a first position and fluid flow through the fluid chamber is not restricted when the internal magnet occupies a second position.

29. A fluid switch according to claim 27 wherein the fluid chamber includes a catheter having the fluid inlet and the fluid outlet and wherein the internal magnet is moveable such that displacement of the internal magnet restricts the flow of fluid through the catheter.

30. A fluid switch according to claim 29, further comprising:
an external magnet for disposition on the skin of a subject, the external magnet providing a magnetic field for displacing the internal magnet such that fluid flow through the catheter is restricted when the internal magnet occupies a first position and fluid flow through the catheter is not restricted when the internal magnet occupies a second position.

* * * * *